United States Patent [19]

Stein et al.

[11] 4,238,484
[45] Dec. 9, 1980

[54] MOLLUSCICIDE COMPOSITIONS AND METHODS OF USE

[75] Inventors: Robert G. Stein, Kenosha, Wis.; Terry L. Couch, Waukegan; Aldo J. Crovetti, Lake Forest, both of Ill.

[73] Assignee: Abbott Laboratories, North Chicago, Ill.

[21] Appl. No.: 33,598

[22] Filed: Apr. 27, 1979

Related U.S. Application Data

[63] Continuation-in-part of Ser. No. 960,819, Nov. 15, 1978, abandoned.

[51] Int. Cl.³ .................... A01N 43/00; A01N 57/00; A01N 57/16
[52] U.S. Cl. .................... 424/202; 424/244
[58] Field of Search .................... 424/202, 244

[56] References Cited

U.S. PATENT DOCUMENTS

2,770,617  11/1956  Marxer .......................... 260/239 EQ
3,639,537  2/1972  Kaufman .......................... 424/202

OTHER PUBLICATIONS

Chemical Abstracts, vol. 70 (1969), p. 10608p.

*Primary Examiner*—Leonard Schenkman
*Attorney, Agent, or Firm*—Paul D. Burgauer; Robert L. Niblack

[57] ABSTRACT

This invention provides a method for the control of mollusks by treating said mollusk or its habitat with a synergistic composition including O,O-dialkyl-O-(3-benzothienglyoxylonitrile oximino)phosphate of the structure

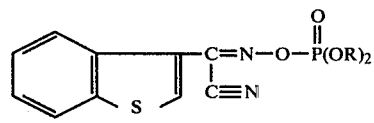

wherein each R is an alkyl group of 1–4 carbon atoms and at least one other known molluscicide.

10 Claims, No Drawings

MOLLUSCICIDE COMPOSITIONS AND METHODS OF USE

HISTORY OF APPLICATION

This application is a continuation-in-part of our application, Ser. No. 960,819, filed Nov. 15, 1978 now abandoned.

BACKGROUND OF THE INVENTION

This invention relates to molluscicides, and more particularly to a combination of molluscicides which act in a synergistic manner to effectively control the growth and life of mollusks.

Many mollusks, including snails and slugs, terrestrial as well as aquatic cause serious economic and health problems in many parts of the world. Snails which are members of a large class of gastropod mullusks, including most forms having a univalve shell or having no shell can be quite injurious to vegetation as they destroy many varieties of beneficial agricultural plants. Even more harmful is the role that they play in the life cycle of many tropical and semitropical diseases. Millions of people and countless animals in many parts of the world are afflicted with these diseases. Snails play a significant role in the growth cycle of the parasite involved in these diseases. With snails, the parasite's larval stage develops and emerges. The latter enters warm-blooded animals where it matures into worms. The worms in turn lay eggs which are carried to vital organs in the animal body by the blood stream. Lastly, the eggs find their way back to the snails through water supplies and the like and the cycle begins once again. Thus, a single snail can be the ancestor of many millions of new snails per year.

For example, snails of the genre Oncomelania, Australorbis and Bulinus are schistosome intermediate hosts. Likewise, snails of the genre Lymnaea are intermediate hosts for the liver flukeworm. Snails of these types particularly cause debilitating human problems. Specifically, bilharziasis has long been endemic in various parts of the world, and is even on the increase.

While various methods of combating bilharziasis and other diseases of this type have been suggested, the destruction of the intermediate snail hosts by toxic chemicals appear to be the most rapid and effective means for reducing transmission of many tropical and semitropical diseases.

However, many chemicals useful in combating mollusks (molluscicides) such as snails have certain disadvantages. In some cases they are difficult to formulate and in certain types of habitats, the available formulations cannot be effectively dispersed. In other instances, the chemical itself is irritating and potentially dangerous to the handler, or it is required to be used at relatively high dosages. In still other instances, it is prematurely absorbed by the soil or other organic materials. Also, some molluscicides currently on the market are ineffective at a high pH, are corrosive to equipment, or their activity is reduced by bright sunlight. Lastly, some molluscicides, while sufficiently active, are inactivated at a low pH and/or do not kill snail eggs.

There is, therefore, the need to provide an effective molluscicide which will not have these side effects, but will directly and surely kill snail eggs upon the treatment of the snails or their habitat.

DETAILED DESCRIPTION OF THE INVENTION

In accordance with the present invention, a new combination molluscicide has been discovered which exhibits synergistic activity against snails and related mollusks. Essentially, the mollusks are controlled by subjecting them to the effect of a synergistic composition which contains a 0,0-dialkyl-0-(3-benzothienglyoxylonitrile oximino)phosphate of the structure

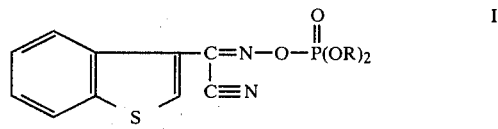

wherein R is a loweralkyl radical of 1–4 carbon atoms, together with a known molluscicide such as 2,5-bis(1-aziridinyl)-p-benzoquinone (hereinafter referred to as ABQ), N-trityl-morpholine, niclosamide [N-(2'-chloro-4'-nitrophenyl)-5-chlorosalicylamide], pentachlorophenol, triphenyltin acetate, 3,5-dibromo-N-(4-bromophenyl)-2-hydroxybenzamide or the like. For the purpose of this invention, "known" molluscicide also includes a mixture of such previously known materials.

All of these compounds except I have recognized molluscicidal activity. However, according to the present invention, the combination of I with at least one other molluscicide produces a highly synergistic effect resulting in a product of much more efficiency, allowing combating of snails at a very low concentration.

The combined and integrated properties of the current molluscicide composition including I provides a more effective and complete means of killing mollusks such as snails and their eggs, requiring only a small amount of each component. Also, the time in which the new combination molluscicide effectively kills and destroys mollusks is greater reduced. Generally, mollusks are destroyed within a 24 hour period after they, or their habitat, have been treated with this new combination molluscicide. Thus, the combination or mixture of these two molluscicides is synergistic in effect and provides a highly practical means of combating mollusks.

The combination molluscicide of the present invention is made quite simply by combining the desired proportions of the individual components. For example, the desired amount of I is mixed with the desired amount of a standard second molluscicide and the combination is added to a diluent or carrier in an application tank or apparatus for application on or treatment of the mollusks and/or their habitat. The two molluscicides may be mixed with each other in a variety of proportions, for example, in equal parts or in a ratio where I is present at twice or half of the amount by weight of the other. As a typical example, good results are obtained with 0.0125 ppm of I and 0.0125 ppm of ABQ in the new combination molluscicide, or one may use 0.020 ppm of one of the above components and 0.01 ppm of the other in the new molluscicide combination. The combination which is found to be generally most effective is a mixture of equal proportions of I with another molluscicide.

The following examples will further illustrate the present invention and its advantages in the treatment and disposal of various mollusks.

EXAMPLE 1

3-Benzothienglyoxylonitrile Oxime

To an ice cooled solution of 3 g. sodium dissolved in 200 ml. ethanol was added dropwise 20 g. of 3-benzothiophene acetonitrile followed by 12.4 g. butyl nitrite. The mixture was stirred for 30 minutes at which time 300 ml. of diethyl ether was added and the mixture was filtered. The mixture of oxime salts (15 g.) was used in the next step. A small sample of the salt was dissolved in water and this solution was acidified with 6 N hydrochloric acid. The mixture was filtered, washed with water and dried. One recrystallization from benzene gave a tan solid, m.p. 142-148 degrees C., identified as 3-benzothienglyoxylonitrile oxime by micro-analysis.

EXAMPLE 2

O,O-Diethyl-O-(3-Benzothienglyoxylonitrile oximino) Phosphate

To a stirring mixture of 11.15 g. 3-benzothienglyoxylonitrile sodium salt in 100 ml. acetone was added 7.74 g. diethyl chlorophosphate. The mixture was stirred one hour and then concentrated to dryness in vacuo. After adding 100 ml. of water, the mixture was extracted several times with ether. The combined ether extracts were washed with water and dried over magnesium sulfate. The drying agent was removed and the solution was concentrated to dryness. A recrystallization from pentane gave 11.6 g. of O,O-diethyl-O-(3-benzothienglyoxylonitrile oximino) phosphate, m.p. 70-72 degress C.

By use of other dialkyl chlorophosphates in equimolar amounts to the above diethyl chlorophosphates, the O,O-dimethyl, O,O-dipropyl or O,O-dibutyl analogs of this compound can be prepared in identical fashion.

EXAMPLE 3

1,4-Diaziridino Benzoquinone

A mixture of 50 g. of cuprous acetate in 500 ml. of methanol was slurried at 20–25 degrees C. while adding 54 g. of ethyleneimine. The temperature was maintained by using an ice-bath. Air was then bubbled through the blue solution and 27.0 g. of 4-benzoquinone in 1000 ml. of methanol was then added while maintaining the same temperature. After stirring for 30 minutes, the resulting orange product was filtered, washed with methanol and then with water. After oven-drying under vacuum, the procuct was identified by microanalysis to be 1,4-diaziridino-p-benzoquinone, m.p. 208-210 degrees C. (decomposition).

EXAMPLE 4

The effect of the present molluscicide combination of I (R=ethyl) and II was compared with the effectiveness of similarly structured and related analogues of I (R=ethyl) against adult and juvenile (A&J) or against newly hatched (NH) B. glabrata (snails). In the various runs, carried out concurrently, the new combination molluscicides were prepared by the combining of equal parts of I (R as shown) and II. In the tests, the type of water used with the molluscicides was dechlorinated tap water (DTW) with a pH of 7.0 at a temperature of 24 degrees C. The snails treated were exposed to the test compounds for a period of 24 hours and a recovery period of 24 hours was provided following the wash in DTW. The results of the tests and provided in the following table.

TABLE

| Compound Concentration | A&J 10 | NH | A&J 1 | NH | A&J 0.1 | NH | A&J 0.025 | NH | Snails ppm |
|---|---|---|---|---|---|---|---|---|---|
| I (R = ethyl) | 8/10 | 10/10 | 0/10 | 10/10 | | | | | |
| ABQ | 10/10 | 10/10 | 10/10 | 10/10 | 0/10 | 4/10 | | | |
| ABQ + I (R = ethyl) | | | 10/10 | 10/10 | 10/10 | 10/10 | 10/10 | 10/10 | |

In the above table, the second number indicates the number of snails in the test; the first number shows the number of dead snails after the test. As can be seen, a synergistic effect is produced by the combination of equal parts of the molluscicides I and ABQ. All snails were killed at the combined concentration of 0.025 ppm. This means that each component was present at only 0.0125 ppm. The lowest effective concentration of I or ABQ separately, was 10 ppm and about 0.5 ppm, respectively.

The results of the above table do not change in a meaningful fashion when the above I is replaced by the homologs wherein R is methyl, isopropyl, butyl or tert.butyl, or when ABQ is replaced by equal parts of pentachlorophenol, N-tritylmorpholine or niclosamide.

In practicing the present invention, any of the various techniques or methods can be employed that have been used to combat mollusks. For example, bait formulations containing the new composition can be prepared such that snails will seek out the treated bait. For application to a body of water for control of aquatic species, effective ratios of I and another molluscicide may be added directly thereto. Any suitable means for effecting the dissemination can be used; for example, formulations of the above combination can be stirred into the water, injected in a portion of the water wherein the water is in turbulent flow, or other mechanical means can be used. The disseminiation can also be effected through the use of a highly hydrophilic surface-active agent, such as water-soluble, non-ionic, surface-active agents, or water-soluble, anionic, surface-active agents.

The combination of I with another molluscicide is so highly effective because component I causes the mollusk to protrude out of its shell, thereby exposing a much larger portion of its lipophylic surface to the other component of the combination molluscicide. The effect of single component I is that of an anaesthetic, exhibited by the fact that the snail's exposed surface can be poked with a pencil without causing its withdrawal into the shell. This phenomenon is reversible by placing the snail in tap water following its exposure to I alone. The snail withdraws into the shell again upon touching by a foreign object. While under the influence of I, the lipophylic body of the snail is a prime target for the other molluscicide component in the new combination molluscicide, causing highly increased absorption of said second component and its killing effect.

Aqueous dispersions in which the particles of said synergistic combination are 5 microns or less in diameter, preferably less than 1 micron in diameter, and more particularly of colloidal dimensions, exhibit the desired molluscicidal activity. Such dispersions may be prepared by any suitable method known in the art. A particularly suitable method comprises pouring a concentrated solution of the new combination molluscicide and a dispersing agent in a water-miscible solvent into the body of water infested with snails, i.e., a river, pond, irrigation canal, etc. These solutions and the aqueous dispersions obtained on diluting them with water are typical compositions of the invention. The water-miscible solvent, may for example, be a water soluble aliphatic ketone such as acetone or methyl ethyl ketone, a water-soluble alcohol such as methyl, ethyl or isopropyl alcohol, dimethylformamide or ethyl oxalate. The dispersing agent suitably constitutes 5 to 20 percent by weight of the solution and preferably 5 to 10 percent by weight thereof. The dispersing agent used may be non-ionic, for example, the polyalkylene oxide condensation products of alkylphenols, more particularly, the condensation product of octylphenol with 8 to 10 molecular proportions of ethylene oxide; or ionic, for example, the sodium salts of secondary alkyl sulfuric acid esters containing 10 to 20 carbon atoms in the alkyl group, or sodium salts of sulfonates of alkylaryl polyethers, or salts (particularly calcium salts) of alkylaryl sulfonates such as calcium dodecylbenzene sulfonate. Mixtures of non-ionic and ionic dispersing agents may also be used.

The compositions of the invention may also be emulsifiable concentrates comprising a solution or dispersion of the above mixture in a water-immiscible, organic liquid and an emulsifying agent. These compositions form more or less stable emulsions on addition to water. The water-immiscible, organic liquid used may be, for example, a hydrocarbon such as toluene, xylene, a mineral oil such as kerosine, or a petroleum horticultural spray oil or a chlorinated hydrocarbon such as a chlorinated benzene, carbon tetrachloride or trichloroethylene. The emulsifying agents may be of the types described above.

The compositions of the invention may also be in the form of a wettable powder, comprising the above active mixture in finely divided form and a dispersing agent such as lignin sulfonates or polyacrylates, or a dispersing agent and a wetting agent such as sodium lauryl sulfate, sodium-N-methyl-N-oleyl laurate, sodium salts of petroleum sulphonates, sodium dioctyl sulphosuccinate, sulfonated esters of fatty alcohols, sodium salts of alkyl benzene sulfonates. A finely divided solid adsorbent carrier for example, adsorbent clay or synthetic silica, may be incorporated in the composition. If there is danger that the carrier employed may affect adversely affect the stability of the compound during storage of the wettable powder, it may be desirable to incorporate a stabilizing agent.

The composition of the invention may also be in the form of granules, pellets, tablets, blocks or thin sheets comprising compound I and the other compound together with a solid carrier. Other useful forms may be prepared by impregnating an absorbent carrier such as porous tiles, clay granules, corn germ cakes or fibrous material such as paper or cloth with a solution of the new combination molluscicide or a mixture thereof. The finely adsorbent carrier is then granulated or pelleted by methods well known in the art. A thermoplastic or fusible resinous carrier may also be employed to produce useful composites. To accomplish this, the new combination is dissolved in a molten resinous carrier and the mixture is subsequently granulated or pelleted. Alternatively, a resinous carrier which is soluble in an organic solvent may be used, the new mixture being dissolved in the solution of the resin, the solvent is then evaporated and the residue is granulated. These composites may be used against either aquatic or terrestrial mollusks.

The concentration of the new molluscicidal mixture to be used with the above carriers is dependent upon many factors, including the carrier employed, the method and conditions of application, and the mollusk species to be controlled. Proper consideration and resolution of these factors are within the skill of those versed in the molluscicide art. Since the mixtures of this invention are effective in a concentration of from about 0.001 to 1.0% by weight of the new mixture, excellent active mixture/carrier combinations comprise those forms wherein the active molluscicide mixture constitutes 1–50% of the total weight. Where only 1% of the active new molluscicidal composition is present, the active mixture/carrier combination can be used as such; when 2–50% by weight of the active new mixture is present, such combination is primarily used as a concentrate which is intended primarily for shipping and storing with the intention to dilute it before use. For use as liquid or solid concentrates, those containing 5–25% by weight of the new combination are preferred.

The compositions of the invention may be used in conjunction with, or have incorporated in them, an attractant or bait for the mollusk. The current molluscicide mixture suitably contains 0.25 to 1 percent by weight of the attractant or bait although lower or higher concentrations may be used.

The composition of the invention containing no attractant or bait are preferably used in such a fashion that upon its dispersion in water, 0.05 to 1.0 parts by weight of the new mixture is present per million parts of water, though higher concentrations may be used if desired. At least about 0.025 parts of the mixture per million parts by weight of the water treated generally is required to effect control of aquatic snails within a reasonable time, and ordinarily no more than about 1 part per million of the mixture will be required. A fundamental advantage of the compositions comprising a bait in addition to the new mixture is that the new mixture's content is not related to the volume of water to which the composition is applied.

The molluscicides of this invention can be employed alone, or in combination with other biologically actice compounds, such as insecticides, fungicides, weed killers (particularly aquatic weed killers to destroy vegetation on which the snails can climb to avoid molluscicide in water), fertilizers, etc. The new molluscicides are not merely specific against certain distinct mollusks, but will be effective against all snails and slugs, and mollusks generally, including, for example, species of Australoís, such as *A. quadelupensis,* species of Bulinus, such as *B. truncatus, B. angolensis* and *B. glabratus,* species of Tropicorpus, such as *T. centrimetralis,* species of Limnae, such as *L. natalensis, L. bulimoides,* and *L. auricularia,* species of Biophalaria, species of Galba, species of Oncomelania, species of Taphius, such as *T. glabratus,* species of Helisoma such as *H. trivolvis,* species of Marisa, such as *M. cornuarietis,* species of Pomacea, such as *P. lineata* and *P. glauca,* and species of Ocinebra, such as *O. japonica.*

We claim:

1. A method for controlling mollusks, comprising applying to the mollusks or their habitat a molluscicidally effective composition containing a 0,0-diloweralkyl-0-(3-benzothienglyoxylonitrile oximino)-phosphate, wherein said loweralkyl contains 1-4 carbons, in combination with a known molluscicide in a ratio of between 2:1 and 1:2 on a weight basis.

2. The method of claim 1 wherein said ratio is about 1:1.

3. The method of claim 1 wherein said known molluscicide is 2,5-bis(1-aziridinyl)-p-benzoquinone.

4. The method of claim 1 wherein said alkyl is ethyl and said know molluscicide is 2,5-bis(1-aziridinyl)-p-benzoquinone.

5. The method of claim 4 wherein said phosphate and said benzoquinone are present in a weight ratio of about 1:1.

6. A molluscicidal composition containing, as the active ingredients, a O,O-diloweralkyl-O-(3-benzothienglyoxylonitrile oximino)phosphate, wherein said loweralkyl contains 1-4 carbons, in combination with a known molluscicide in a ratio of between 2:1 and 1:2 on a weight basis.

7. The composition of claim 6 wherein said known molluscicide is 2,5-bis(1-aziridinyl)-p-benzoquinone.

8. The composition of claim 7 wherein said ingredients are present in a weight ratio of about 1:1.

9. The composition of claim 8 wherein said ingredients are combined with a suitable liquid or solid diluent.

10. The composition of claim 9 wherein said diluent is an emulsifiable concentrate containing 1-5% by weight of said combination.

* * * * *